(12) United States Patent
Long et al.

(10) Patent No.: US 11,357,393 B2
(45) Date of Patent: Jun. 14, 2022

(54) ENDOSCOPE

(71) Applicant: Wuhan Youcare Technology Co., Ltd., Wuhan (CN)

(72) Inventors: Gang Long, Wuhan (CN); Xuecheng Hu, Wuhan (CN); Jinping Li, Wuhan (CN); Shaogang Wang, Wuhan (CN); Junhui Zhang, Wuhan (CN); Jianxing Li, Wuhan (CN); Yaohui Wu, Wuhan (CN); Yeyun Mao, Wuhan (CN)

(73) Assignee: WUHAN YOUCARE TECHNOLOGY CO., LTD., Wuhan (CN)

( * ) Notice: Subject to any disclaimer, the term of this patent is extended or adjusted under 35 U.S.C. 154(b) by 239 days.

(21) Appl. No.: 16/686,202

(22) Filed: Nov. 17, 2019

(65) Prior Publication Data
US 2020/0077874 A1 Mar. 12, 2020

Related U.S. Application Data

(63) Continuation-in-part of application No. PCT/CN2017/092575, filed on Jul. 12, 2017.

(51) Int. Cl.
| *A61B 1/00* | (2006.01) |
| *A61B 1/018* | (2006.01) |
| *A61B 1/005* | (2006.01) |
| *A61B 1/01* | (2006.01) |
| *A61B 1/015* | (2006.01) |
| *A61B 1/06* | (2006.01) |

(52) U.S. Cl.
CPC ............ *A61B 1/018* (2013.01); *A61B 1/0052* (2013.01); *A61B 1/0057* (2013.01); *A61B 1/00135* (2013.01); *A61B 1/01* (2013.01); *A61B 1/015* (2013.01); *A61B 1/06* (2013.01)

(58) Field of Classification Search
None
See application file for complete search history.

(56) References Cited

U.S. PATENT DOCUMENTS

| 5,301,061 A * | 4/1994 | Nakada | A61B 1/00059 348/75 |
| 5,846,221 A * | 12/1998 | Snoke | A61B 1/0052 604/500 |
| 2005/0080342 A1 * | 4/2005 | Gilreath | A61B 1/05 600/476 |

(Continued)

*Primary Examiner* — Timothy J Neal
(74) *Attorney, Agent, or Firm* — Matthias Scholl P.C.; Matthias Scholl

(57) ABSTRACT

An endoscope, including: a handle, a sheath tube, an endoscopic cannula, and a tensioning mechanism. The sheath tube includes a first axial guide hole and a first joint pin disposed in the first axial guide hole. The handle includes a second axial guide hole and a second joint pin disposed in the second axial guide hole. The first joint pin matches and is directly connected to the second joint pin. The sheath tube matches and connects to the handle. The handle includes a cavity and the tensioning mechanism is disposed in the cavity. The endoscopic cannula includes a flexible part extending out of the sheath tube and a rigid part fixed in the sheath tube. The flexible part includes a steering wire. The first joint pin is connected to the steering wire. The tensioning mechanism is connected to the second joint pin.

9 Claims, 10 Drawing Sheets

(56) References Cited

U.S. PATENT DOCUMENTS

| | | | |
|---|---|---|---|
| 2005/0085692 A1* | 4/2005 | Kiehn | A61B 1/00105 600/130 |
| 2006/0276690 A1* | 12/2006 | Farris | A61B 1/00117 600/162 |
| 2010/0280311 A1* | 11/2010 | McGrath | A61B 1/00137 600/104 |
| 2012/0016191 A1* | 1/2012 | Ito | A61B 1/00105 600/104 |
| 2016/0088999 A1* | 3/2016 | Langell | A61B 5/7246 348/68 |
| 2017/0215706 A1* | 8/2017 | Harrah | A61B 1/00117 |

* cited by examiner

ENDOSCOPE

CROSS-REFERENCE TO RELATED APPLICATIONS

This application is a continuation-in-part of International Patent Application No. PCT/CN2017/092575 with an international filing date of Jul. 12, 2017, designating the United States, now pending, and further claims foreign priority benefits to Chinese Patent Application No. 201710346309.X filed May 17, 2017. The contents of all of the aforementioned applications, including any intervening amendments thereto, are incorporated herein by reference.

BACKGROUND

The disclosure relates to a modular endoscope.

An endoscope is an optical instrument used to look into the body.

A conventional endoscope is an integrated structure including an image sensor, an optical lens, a light source, treatment equipment, and a sheath tube. To facilitate the clinical observation and treatment, the sheath tube is provided with a bending mechanism, a stretching mechanism and a rotating mechanism. This makes the endoscope bulky and expensive.

SUMMARY

The disclosure provides a modular endoscope.

Provided is an endoscope, comprising: a handle, a sheath tube, an endoscopic cannula, and a tensioning mechanism.

The sheath tube comprises a first axial guide hole, a first joint pin disposed in the first axial guide hole and capable of axially moving in the first axial guide hole; the handle comprises a second axial guide hole, a second joint pin disposed in the second axial guide hole and capable of axially moving in the second axial guide hole; the damping force between the first axial guide hole and the first joint pin and the damping force between the second axial guide hole and the second joint pin are both larger than a clamping force between the first joint pin and the second joint pin; the first joint pin matches and is directly connected to the second joint pin; the sheath tube matches and connects to the handle; the handle comprises a cavity and the tensioning mechanism is disposed in the cavity to axially tension the second joint pin; the endoscopic cannula comprises a flexible part extending out of the sheath tube and a rigid part fixed in the sheath tube; the flexible part comprises a steering wire, and the first joint pin is connected to the steering wire via a wire line; and the tensioning mechanism is connected to the second joint pin.

The tensioning mechanism can comprise a driving lever fixedly connected to the second joint pin via the wire line; the handle can comprise a thumbwheel connected to the driving lever.

The sheath tube can comprise a hollow conical sleeve comprising an axial hole, a cylindrical transition section, and a first joint sleeve; the endoscopic cannula can be fixed in the axial hole of the hollow conical sleeve; the cylindrical transition section can be disposed between the hollow conical sleeve and the first joint sleeve; the first joint sleeve can comprise the first axial guide hole, and the first joint pin can be disposed in the first axial guide hole; the handle can be a hollow structure and can comprise a second joint sleeve; the second joint sleeve can comprise the axial second guide hole, and the second joint pin can be disposed in the second axial guide hole.

The endoscopic cannula can be a three-channel tube comprising a light source channel, an instrument channel and a feeder channel; the cylindrical transition section can comprise an outer wall equipped with a first three-way pipe communicating with the light source channel and a second three-way pipe communicating with the instrument channel; and the hollow conical sleeve of the sheath tube can comprise an outer wall having a through hole for water injection.

The second joint pin can comprise a shaft lever; the shaft lever can comprise a first end provided with two radially symmetrically disposed fixing pins; the first joint pin can comprise a sleeve tube, and the first end of the shaft lever can be disposed in the sleeve tube; the sleeve tube can comprise a circumferential wall provided with two first locating slots receiving the two fixing pins; and the two first locating slots are L-shaped.

The second joint sleeve can be a cylinder comprising an inner wall having two symmetrically disposed first protrusions; the first joint sleeve can be a cylinder comprising two second locating slots to receive the two symmetrically disposed first protrusions to axially fix the first joint sleeve and the second joint sleeve; and the two second locating slots are L-shaped.

The first joint pin can comprise a first terminal and a first radial slot next to the first terminal, and the second joint pin can comprise a second terminal and a second radial slot next to the second terminal; the first terminal can be embedded in the second radial slot, and the second terminal can be embedded in the first radial slot; a diameter of the first joint pin can be the same as that of the second joint pin, and an outer surface of the first joint pin can be coincident to that of the second joint pin.

The first joint sleeve can comprise a first stepped end, and the second joint sleeve can comprise a second stepped end corresponding to the first stepped end in shape; the first stepped end can comprise two abreast L-shaped second protrusions extending vertically with respect to an axis of the first joint sleeve; the second stepped end can comprise two third locating slots corresponding to the two L-shaped second protrusions in shape; and an outer surface of the first joint sleeve can be coincident to that of the second joint sleeve.

The endoscope is modular and comprises a sheath tube and a handle which is detachably connected to the sheath tube. The sheath tube is disposable, while the handle is reusable, thus reducing the use cost of the endoscope.

Figure 1:
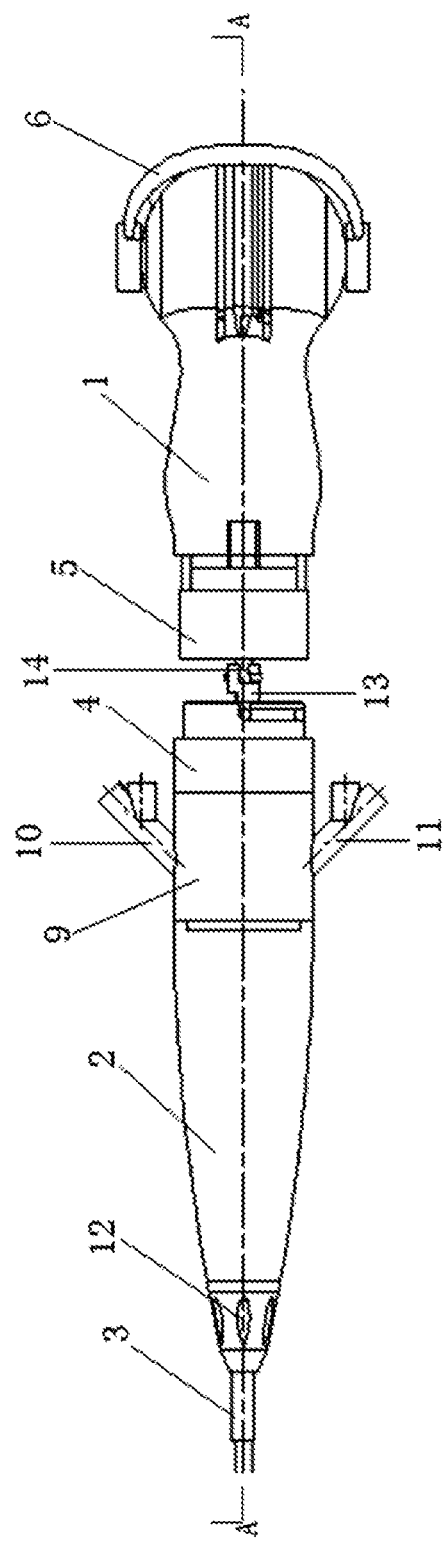
FIG. 1 is a schematic diagram of an endoscope according to one embodiment of the disclosure where the first joint sleeve is separated from the second joint sleeve.
Figure 2:
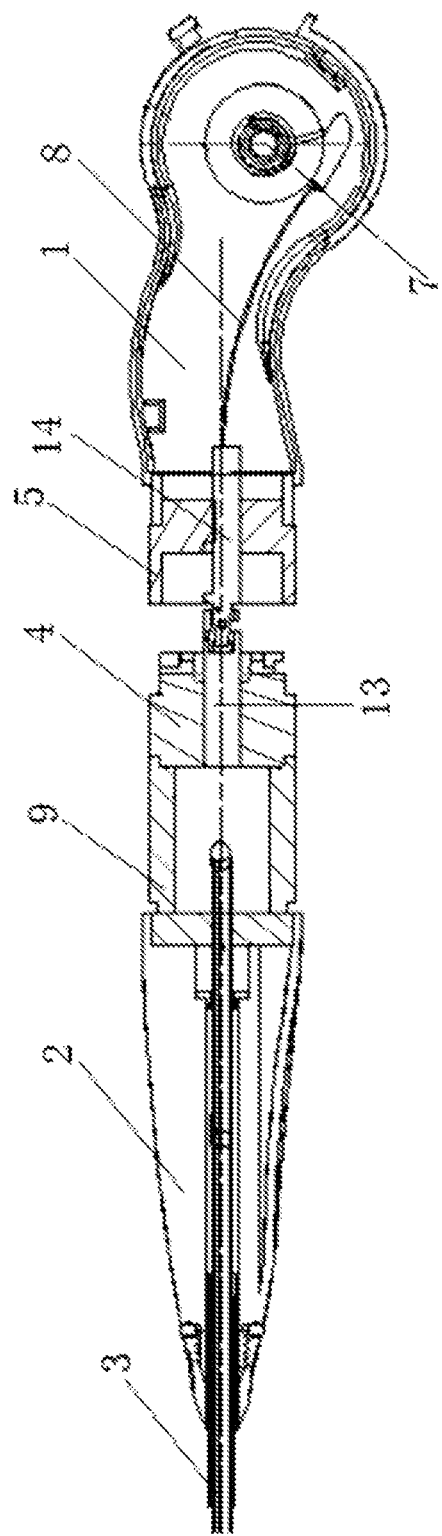
FIG. 2 is a sectional view of an endoscope taken from line A-A in FIG. 1.
Figure 3:
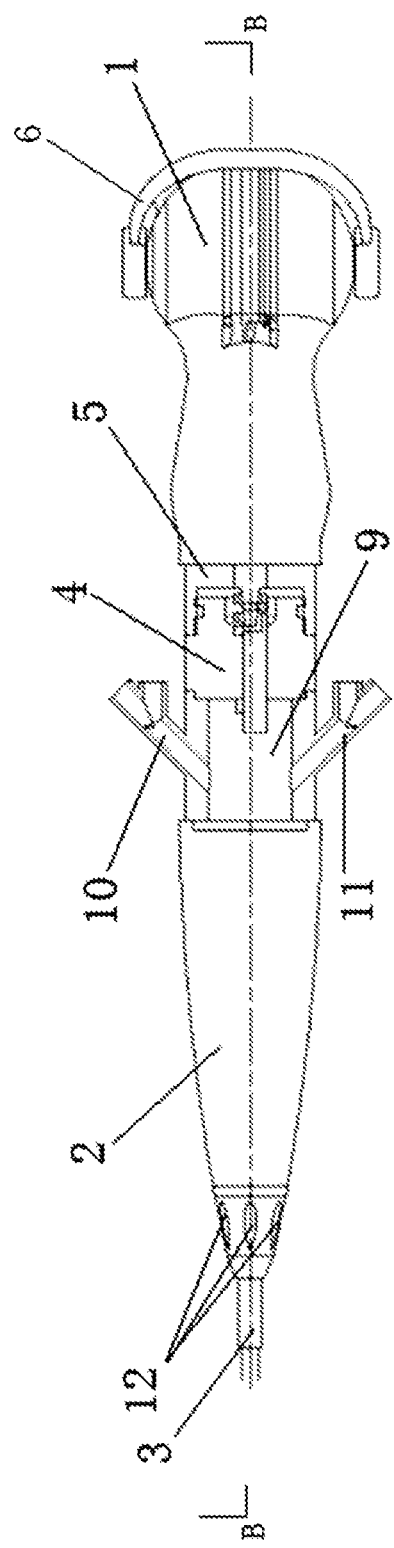
FIG. 3 is a schematic diagram of an endoscope according to one embodiment of the disclosure where the handle is connected to the sheath tube.
Figure 4:
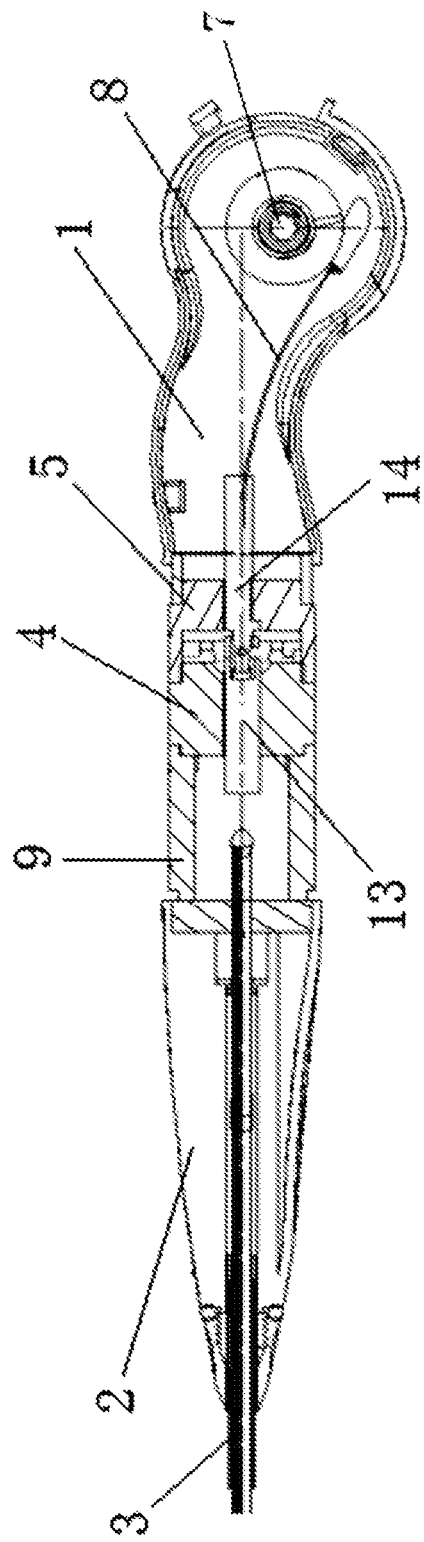
FIG. 4 is a sectional view of an endoscope taken from line B-B in FIG. 3.

In the drawings, the following reference numbers are used: 1. Handle; 2. Sheath tube; 3. Endoscopic cannula; 4. First joint sleeve; 5. Second joint sleeve; 6. Thumbwheel; 7. Driving lever; 8. Wire line; 9. Cylindrical transition section; 10. First three-way pipe; 11. Second three-way pipe; 12. Through hole; 13. First joint pin; 13.1. Sleeve tube; 14. Second joint pin; 14.1. Shaft lever; 14.2. Fixing pin; 15.1. First part; 15.2. Second part; 16. Third locating slot; 17. First protrusion; 18.1. First section; 18.2. Second section; 19. First radial slot; 20. Second radial slot; 21. Second protrusion; 21.1. First connection segment; and 21.2. Second connection segment.

DETAILED DESCRIPTIONS

To further illustrate, embodiments detailing an endoscope are described below. It should be noted that the following embodiments are intended to describe and not to limit the disclosure.

As shown in FIGS. 1-6, an endoscope comprises a handle 1, a sheath tube 2, and an endoscopic cannula 3. The endoscopic cannula 3 is disposed in the sheath tube 2; the sheath tube 2 is fixedly connected to a cylindrical transition section 9; the cylindrical transition section 9 is fixedly connected to a first joint sleeve 4; the cylindrical transition section 9 comprises an outer wall equipped with a first three-way pipe 10 communicating with the light source channel and a second three-way pipe 11 communicating with the instrument channel; and the hollow conical sleeve of the sheath tube 2 comprises an outer wall having a through hole 12 connected to a feeder channel. The handle 1 comprises a driving lever 7; the driving lever 7 is connected to a thumbwheel 6; the driving lever 7 is connected to the second joint pin 14 via a wire line 8; the endoscopic cannula 3 is a three-channel tube comprising a light source channel, an instrument channel and a feeder channel, and one end of the endoscopic cannula 3 close to the through hole 12 is a hose; and a first joint pin 13 is connected to the steering wire via a wire line 8.

The first joint pin 13 is disposed in the first joint sleeve 4; an outer surface of the first joint sleeve 4 is coincident to that of the second joint sleeve 5; the handle 1 comprises a second joint sleeve 5; and the second joint sleeve 5 comprises the second joint pin 14.

Example 1

Figure 5:
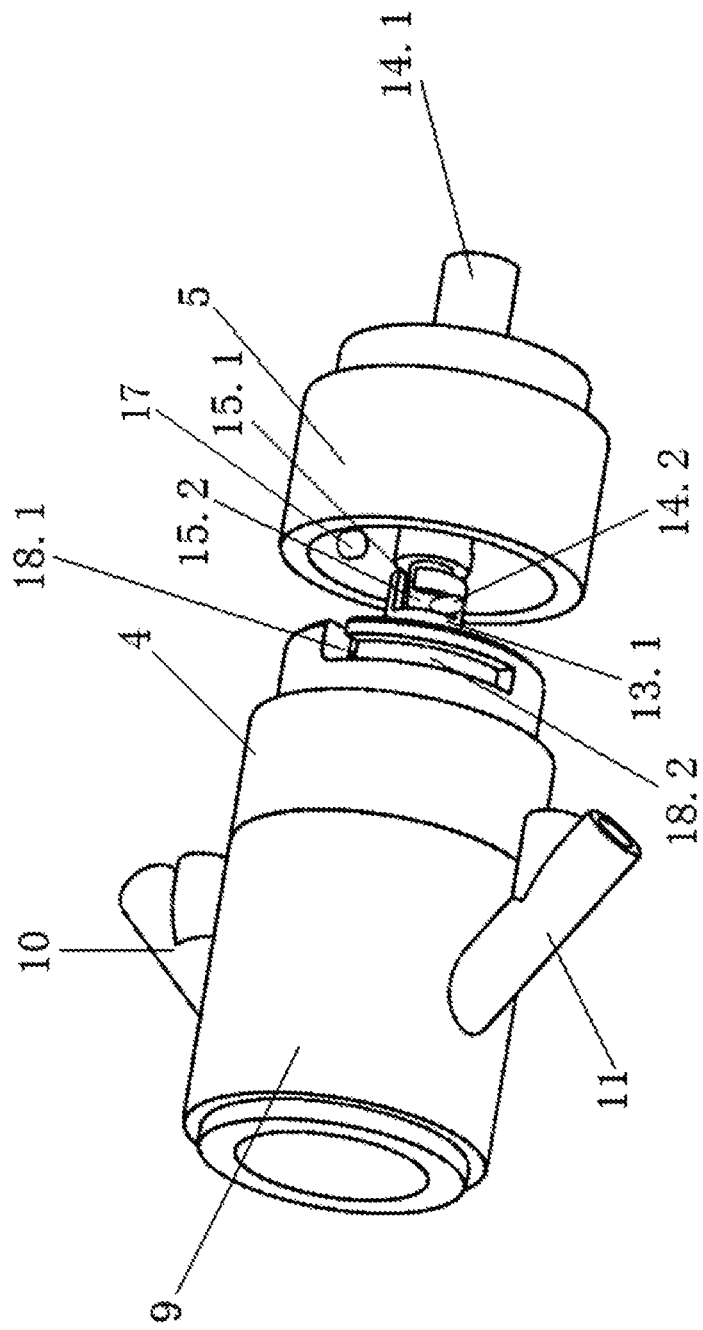
FIG. 5 is a stereogram of a connection of the first joint sleeve and the second joint sleeve of an endoscope according to one embodiment of the disclosure.
Figure 6:
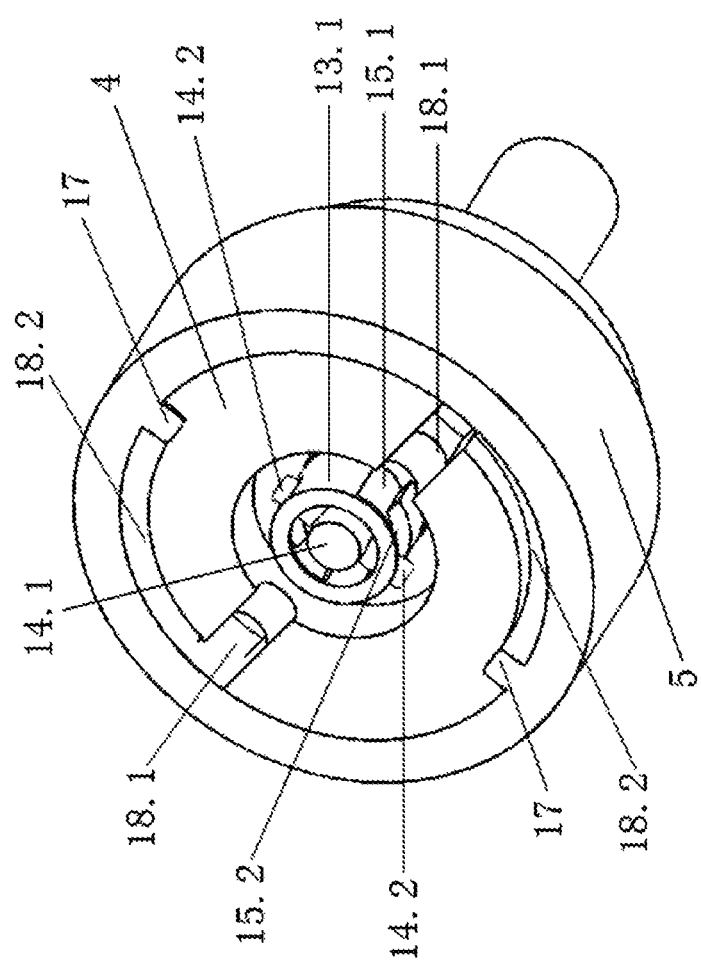
FIG. 6 is a stereogram of the matched first joint sleeve and the second joint sleeve of an endoscope according to one embodiment of the disclosure.
Figure 7:
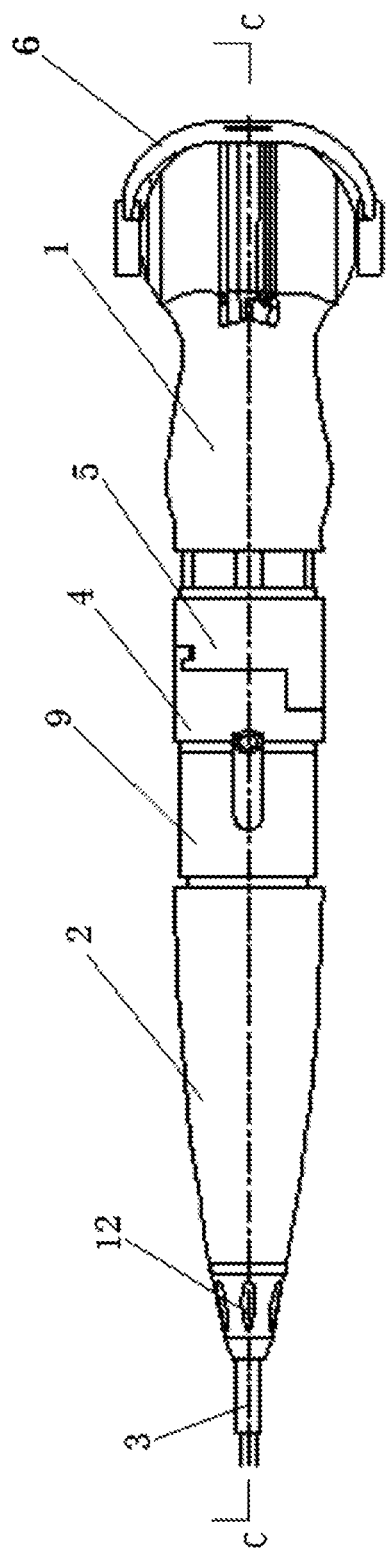
FIG. 7 is a schematic diagram of an endoscope according to another embodiment of the disclosure where the first joint sleeve is connected to the second joint sleeve.
Figure 8:
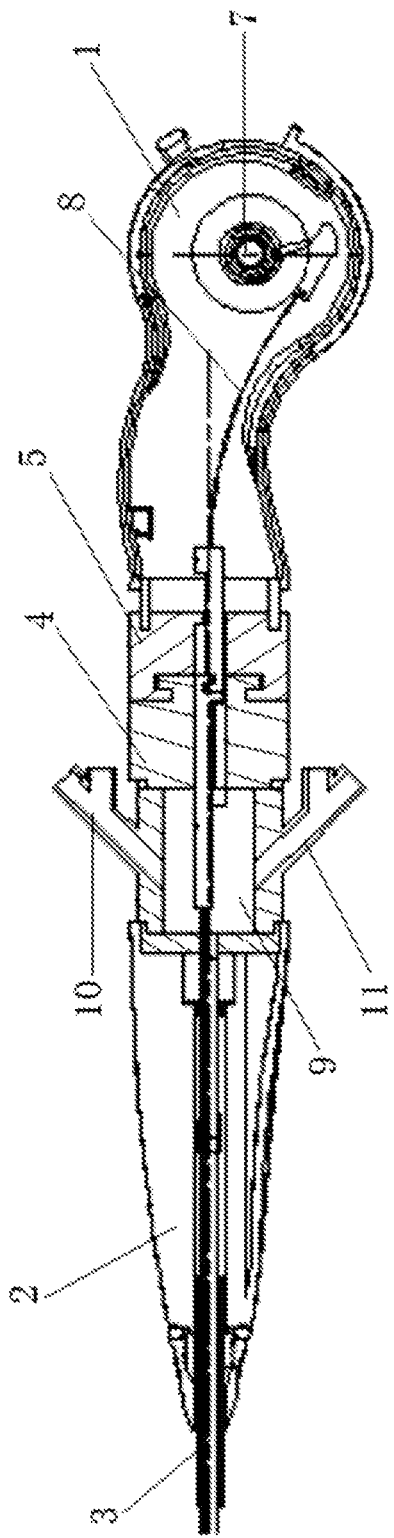
FIG. 8 is a sectional view of an endoscope taken from line C-C in FIG. 7.
Figure 9:
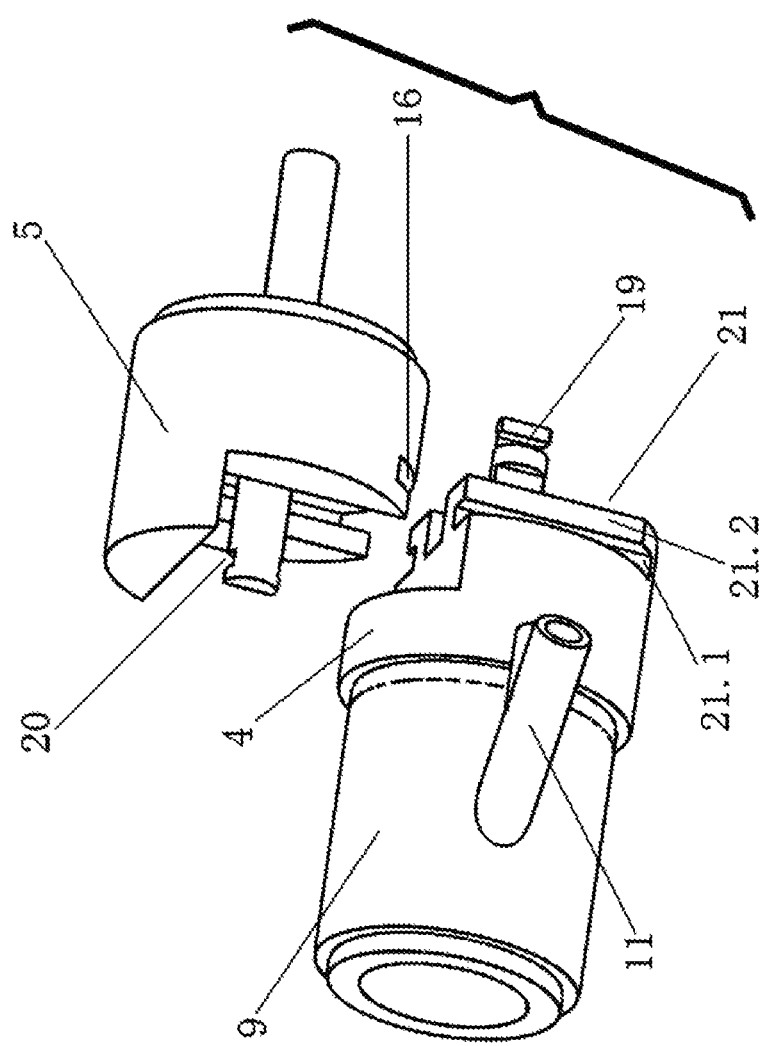
FIG. 9 is an exploded view of a connection of the first joint sleeve and the second joint sleeve of an endoscope according to another embodiment of the disclosure.
Figure 10:
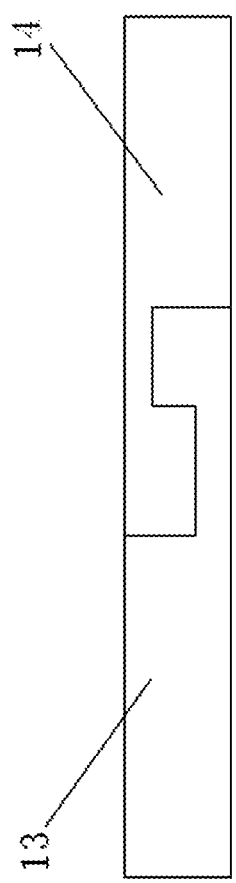
FIG. 10 is a plan sketch of a connection of the first joint pin and the second joint pin of an endoscope according to another embodiment of the disclosure.

As shown in FIGS. 5-6, the second joint pin 14 comprises a shaft lever 14.1; the shaft lever 14.1 comprises a first end provided with two radially symmetrically disposed fixing pins 14.2; the first joint pin 13 comprises a sleeve tube 13.1, and the first end of the shaft lever 14.1 is disposed in the sleeve tube 13.1; the sleeve tube 13.1 comprises a circumferential wall provided with two first locating slots receiving the two fixing pins 14.2; a first locating slot comprises a first part 15.1 and a second part 15.2; the first part is disposed axially on the sleeve tube 13.1; and the second part is connected to the first part and disposed radially on the sleeve tube 13.1, the second joint sleeve 5 is a cylinder comprising an inner wall having two symmetrically disposed first protrusions 17; the first joint sleeve 4 is a cylinder comprising two second locating slots to receive the two symmetrically disposed first protrusions 17 to axially fix the first joint sleeve 4; a second locating slot comprises a first section 18.1 and a second section 18.2; the first section 18.1 is disposed axially on the first joint sleeve 4; and the second section 18.2 is connected to the first section 18.1 and disposed radially on the first joint sleeve 4.

Example 3

As shown in FIGS. 7-10, the first joint pin 13 comprises a first terminal and a first radial slot 19 next to the first terminal, and the second joint pin 14 comprises a second terminal and a second radial slot 20 next to the second terminal; the first terminal is embedded in the second radial slot 20, and the second terminal is embedded in the first radial slot 19; a diameter of the first joint pin 13 is the same as that of the second joint pin 14, and an outer surface of the first joint pin 13 is coincident to that of the second joint pin 14. The first joint sleeve 4 comprises a first stepped end; the first stepped end comprises two abreast L-shaped second protrusions 21 extending vertically with respect to an axis of the first joint sleeve 4; the second protrusions 21 comprises a first connection segment 21.1 and a second connection segment 21.2; the first connection segment 21.1 is vertically disposed to the first joint sleeve 4, and the second connection segment 21.2 is vertically disposed to the first connection segment 21.1 and toward the outer surface of the first joint sleeve 4; the second joint sleeve 5 comprises a second stepped end corresponding to the first stepped end in shape; and the second stepped end comprises two third locating slots 16 corresponding to the two L-shaped second protrusions 21 in shape.

The endoscope of the disclosure comprises a handle 1 and a sheath tube 2; the handle 1 comprises a first cover and a second cover, and the two covers match each other; the handle 1 comprises a driving lever 7; the driving lever 7 is connected to a thumbwheel 6; the driving lever 7 is connected to a wire line 8; the wire line 8 is connected to a second joint pin 14; a first joint pin 13 matches and is directly connected to the second joint pin 14; the first joint pin 13 is connected to the steering wire of a soft sheath in the endoscopic cannula 3. The driving lever 7 drives the second joint pin 14 via the wire line 8, and the second joint pin 14 drives the soft sheath in the endoscopic cannula 3 bending via the first joint pin 13; the sheath tube 2 comprises a cylindrical transition section 9 provided with a three-way pipes connected to the sheath tube 2, the three-way pipes includes a light source channel, an instrument channel and a feeder channel. After the handle 1 is connected with the sheath tube 2, the three-way pipes on the side of the cylindrical transition section 9 are connected to a power interface on a host; a light source is supplied by the power interface via an optical fiber; the optical fiber transfers the light from the light source to a micro CMOS camera; the micro CMOS camera provides certain lighting conditions; the images taken by the camera are transferred from the camera interface to the host via a camera cable; the transferred images are displayed on the screen via an image transmission line.

It will be obvious to those skilled in the art that changes and modifications may be made, and therefore, the aim in the appended claims is to cover all such changes and modifications.

What is claimed is:

1. A device, comprising:
   1) a handle;
   2) a sheath tube;
   3) an endoscopic cannula; and
   4) a tensioning mechanism;
   wherein:
   the sheath tube comprises a first axial guide hole, and a first joint pin disposed in the first axial guide hole and capable of axially moving in the first axial guide hole;
   the handle comprises a second axial guide hole, and a second joint pin disposed in the second axial guide hole and capable of axially moving in the second axial guide hole;
   the sheath tube is detachably connected to the handle via the first joint pin and the second joint pin, wherein the first joint pin is detachably connected to the second joint pin;
   the handle comprises a cavity and the tensioning mechanism is disposed in the cavity to axially tension the second joint pin;
   the endoscopic cannula comprises a flexible part extending out of the sheath tube and a rigid part fixed in the sheath tube;
   the flexible part comprises a steering wire, and the first joint pin is connected to the steering wire via a first wire line; and
   the tensioning mechanism is connected to the second joint pin.

2. The device of claim 1, wherein
   the sheath tube comprises a hollow conical sleeve comprising an axial hole, a cylindrical transition section, and a first joint sleeve; the endoscopic cannula is fixed in the axial hole of the hollow conical sleeve; the cylindrical transition section is disposed between the hollow conical sleeve and the first joint sleeve; the first joint sleeve comprises the first axial guide hole, and the first joint pin is disposed in the first axial guide hole;
   the handle is a hollow structure and comprises a second joint sleeve; the second joint sleeve comprises the axial second guide hole, and the second joint pin is disposed in the second axial guide hole; and
   the first joint sleeve is detachably connected to the second joint sleeve.

3. The device of claim 2, wherein the endoscopic cannula is a three-channel tube comprising a light source channel, an instrument channel and a feeder channel; the cylindrical transition section comprises an outer wall equipped with a first three-way pipe communicating with the light source channel and a second three-way pipe communicating with the instrument channel; and the hollow conical sleeve of the sheath tube comprises an outer wall having a through hole that is connected to the feeder channel for water injection.

4. The device of claim 2, wherein the second joint pin comprises a shaft lever; the shaft lever comprises a first end provided with two radially symmetrically disposed fixing pins; the first joint pin comprises a sleeve tube, and the first end of the shaft lever is disposed in the sleeve tube; the sleeve tube comprises a circumferential wall provided with two first locating slots receiving the two fixing pins; and the two first locating slots are L-shaped.

5. The device of claim 4, wherein the second joint sleeve is a cylinder comprising an inner wall having two symmetrically disposed first protrusions; the first joint sleeve is a cylinder comprising two second locating slots to receive the two symmetrically disposed first protrusions to axially fix the first joint sleeve and the second joint sleeve; and the two second locating slots are L-shaped.

6. The device of claim 2, wherein the first joint pin comprises a first terminal and a first radial slot next to the first terminal, and the second joint pin comprises a second terminal and a second radial slot next to the second terminal; the first terminal is embedded in the second radial slot, and the second terminal is embedded in the first radial slot; a diameter of the first joint pin is the same as that of the second joint pin, and an outer surface of the first joint pin is coincident to that of the second joint pin.

7. The device of claim 6, wherein the first joint sleeve comprises a first stepped end, and the second joint sleeve comprises a second stepped end corresponding to the first stepped end in shape; the first stepped end comprises two abreast L-shaped second protrusions extending vertically with respect to an axis of the first joint sleeve; the second stepped end comprises two third locating slots corresponding to the two L-shaped second protrusions in shape; and an outer surface of the first joint sleeve is coincident to that of the second joint sleeve.

8. The device of claim 1, wherein the tensioning mechanism comprises a driving lever fixedly connected to the second joint pin via a second wire line; the handle comprises a thumbwheel connected to the driving lever.

9. The device of claim 1, wherein when in use, the tensioning mechanism drives the second joint pin to axially move with respect to the second axial guide hole, whereby the first joint pin is axially moved with respect to the first axial guide hole by the second joint pin to stretch or release the steering wire of the flexible part in the endoscopic cannula for changing the bending status of the flexible part in the endoscopic cannula.

* * * * *